United States Patent [19]

Daniels

[11] 4,117,221

[45] Sep. 26, 1978

[54] AMINOACYL DERIVATIVES OF AMINOGLYCOSIDE ANTIBIOTICS

[75] Inventor: Peter J. L. Daniels, Cedar Grove, N.J.

[73] Assignee: Schering Corporation, Kenilworth, N.J.

[21] Appl. No.: 734,166

[22] Filed: Oct. 20, 1976

Related U.S. Application Data

[63] Continuation-in-part of Ser. No. 452,571, Mar. 19, 1974, abandoned.

[51] Int. Cl.² ............................................. C07H 15/22
[52] U.S. Cl. ..................................... 536/17; 424/180; 536/10
[58] Field of Search ................................. 536/17, 10

[56] References Cited

U.S. PATENT DOCUMENTS

| | | | |
|---|---|---|---|
| 3,920,628 | 11/1975 | Daniels | 536/17 |
| 4,002,742 | 1/1977 | Wright et al. | 536/17 |
| 4,029,882 | 6/1977 | Wright | 536/17 |

*Primary Examiner*—Johnnie R. Brown
*Attorney, Agent, or Firm*—Bruce Eisen; Raymond McDonald; Carver C. Joyner

[57] ABSTRACT

Disclosed herein are novel 1-N-X-aminoglycoside antibacterial agents produced from antibiotics elaborated by species of the genus Micromonospora wherein X is a member selected from the group consisting of S-3-amino-2-hydroxypropionyl and S-4-amino-2-hydroxybutyryl and S-5-amino-2-hydroxypentanoyl. Also disclosed are novel intermediates in the production of the foregoing.

46 Claims, No Drawings

AMINOACYL DERIVATIVES OF AMINOGLYCOSIDE ANTIBIOTICS

This application is a continuation-in-part of copending application Ser. No. 452,571 filed Mar. 19, 1974 now abandoned.

This invention relates to semi-synthetic antibacterial agents. More particularly, this invention relates to semi-synthetic aminoglycoside aminocyclitol antibacterial agents prepared from antibiotics elaborated by species of microorganisms from the genus Micromonospora. In particular, this invention relates to semi-synthetic aminoglycoside aminocyclitol anti-bacterial agents wherein the 1-amino group of the aminocyclitol moiety is acylated by a hydroxy aminoacyl group, to the non-toxic acid addition salts of such agents and to methods for producing such compounds.

PRIOR ART

In U.S. Pat. No. 3,780,018, issued Dec. 18, 1973, is described a process whereby 1-[L-(-)-γ-amino-α-hydroxybutyryl]gentamicin $C_1$ and 2'-[L-(-)-γ-amino-α-hydroxybutyryl]gentamicin $C_1$ are prepared by reacting gentamicin $C_1$ with a blocked active ester of L-(-)-γ-amino-α-hydroxybutyric acid (HABA) followed by deblocking via methods known in the art and separation of the reaction mixture by chromatographic means.

I have discovered a novel process for preparing acyl, 1-[L-(-)-β-amino-α-hydroxypropionyl], 1-[L-(-)-γ-amino-α-hydroxybutyryl] and 1-[L-(-)-γ-amino-α-hydroxypentanoyl] derivatives of aminoglycoside antibiotics.

By the process of this invention, I have prepared novel antibacterial agents having surprisingly unexpected properties when compared with the respective underivatized antibiotics. Generally, these novel compounds are active against bacterial and/or protozoan strains. Further, they are active against bacteria which have become substantially insensitive to said underivatized antibiotics. Thus, this invention discloses a plurality of active aminoglycoside antibacterial and/or antiprotozoal agents and a process which is effective for their preparation.

In one of its process aspects, this invention embraces a method for producing 1-N-hydroxyaminoacyl derivatives of the aforementioned antibiotics by a series of steps comprising blocking the more reactive amino groups on an aminoglycoside antibiotic, reacting the blocked compound with a hydroxyaminoacylating agent wherein the amino and hydroxy groups are substituted on different carbon atoms and deblocking the resulting compound.

In another of its process aspects, this invention embraces the production of pharmaceutically acceptable acid addition salts of said 1-N-acyl antibacterial agents by adjusting an aqueous solution of said agent to pH 4.0 followed by lyophilization. The salts produced thereby are the functional equivalent of the free nitrogen base.

In one of its product aspects, this invention may be described as a 1-N-X-aminoglycoside selected from the group consisting of 1-N-X-gentamicin A, 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin X, 1-N-X-sisomicin, 1-N-X-verdamicin, 1-N-X-Antibiotic G-418, 1-N-X-Antibiotic 66-40 B, 1-N-X-Antibiotic 66-40D, 1-N-X-Antibiotic JI-20A, 1-N-X-Antibiotic JI-20B, 1-N-X-Antibiotic G-42, and the pharmaceutically acceptable acid addition salts thereof, wherein X is a member selected from the group consisting of S-3-amino-2-hydroxypropionyl, S-4-amino-2-hydroxybutyryl and S-5-amino-2-hydroxypentanoyl with the proviso that in 1-N-X-gentamicin $C_1$, 1-N-X-gentamicin $C_{1a}$ and 1-N-X-gentamicin $C_2$, X may only be S-3-amino-2-hydroxypropionyl.

In another of its product aspects, this invention relates to valuable intermediates selected from the group consisting of 2'-N-acyl, 6'-N-acyl, or 2',3-di-N-acyl derivatives of the antibiotic starting material. Exemplary of such intermediates are the following: 6'-N-t-butoxycarbonylgentamicin $C_{1a}$, 6'-N-trifluoroacetyl gentamicin B, 6'-N-trifluoroacetyl antibiotic JI-20A, 6'-N-trifluoroacetyl antibiotic 66-40B, 6'-N-trifluoroacetyl antibiotic 66-40D, 6'-N-t-butoxycarbonyl sisomicin. Also included among the valuable intermediates are 2'-N-trifluoroacetyl gentamicin $C_1$ and 2',3-di-N-trifluoroacetyl gentamicin $C_1$.

A preferred group of 1-N-X-aminoglycoside antibacterial agents from the above-defined class consists of 1-N-X-sisomicin, 1-N-X-verdamicin, 1-N-X-antibiotic 66-40B, 1-N-X-antibiotic 66-40D, 1-N-X-gentamicin B and 1-N-X-gentamicin $B_1$.

The underivatized (parent) antibiotics are all known in the art, except gentamicin $C_{2a}$ which is disclosed in application Ser. No. 498,495 filed August 10, 1974, now U.S. Pat. No. 3,984,395 which application is a continuation-in-part of application Ser. No. 269,914 filed July 7, 1972, now abandoned. Both of the applications are entitled "Novel Antibiotics From Micromonospora."

S-5-amino-2-hydroxypentanoic acid is prepared by diazotisation of L-ornithine by the method described by S. Ohshiro et al. in *Yakugaku Zasshi*, 87, 1184 (1967).

As used herein, the terms "blocking group" or "protecting group" refers to groups which render the blocked or protected amino groups inert to subsequent desired chemical manipulation, but which can easily be removed at the end of the synthetic sequence without cleaving the desired N-acyl or N-aminohydroxyacyl group.

Amino protecting groups are generally known in the art. However, for this invention trifluoroacetyl, 2,2,2-trichloroethoxycarbonyl, t-butoxycarbonyl, benzyloxycarbonyl and 4-methoxybenzyloxycarbonyl groups are among those preferred. Particularly preferred from the foregoing are trifluoroacetyl, t-butoxycarbonyl, and benzyloxycarbonyl groups.

In the blocking steps, the protecting group is usually employed in the form of an acid imidazole derivative, and acid azide or as active esters such as ethylthioltrifluoroacetate N-benzyloxycarbonyloxy succinimide or p-nitrophenyltrichloroethyl carbonate. Thus, blocking groups may be described generically as being derived from a compound BgLg wherein Bg becomes the blocking group such as the acid portion of an active ester, and Lg is a leaving group such as imidazole.

The acylating agents and hydroxyaminoacylating agents employed in the process of this invention are used in the form of active esters or acid azides or acid imidazole derivatives each of which has been previously exemplified. Further, in those instances wherein the acylating agent has an amino substituent, the amino group is blocked. Thus, when the hydroxyaminoacyl product desired is iso-serinyl, the acylating agent would take the form of

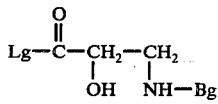

wherein the carboxyl function is preferably activated in the form of an active ester (Lg) and the amino is preferably blocked by a benzyloxy carbonyl group which is facilely removed by hydrogenolysis or a t-butoxycarbonyl group or a trifluoroacetyl group the former being conveniently removed with acid and the latter with base.

The following reaction sequences and examples are set forth to facilitate the teaching of this invention but should not be interpreted as limiting the scope thereof.

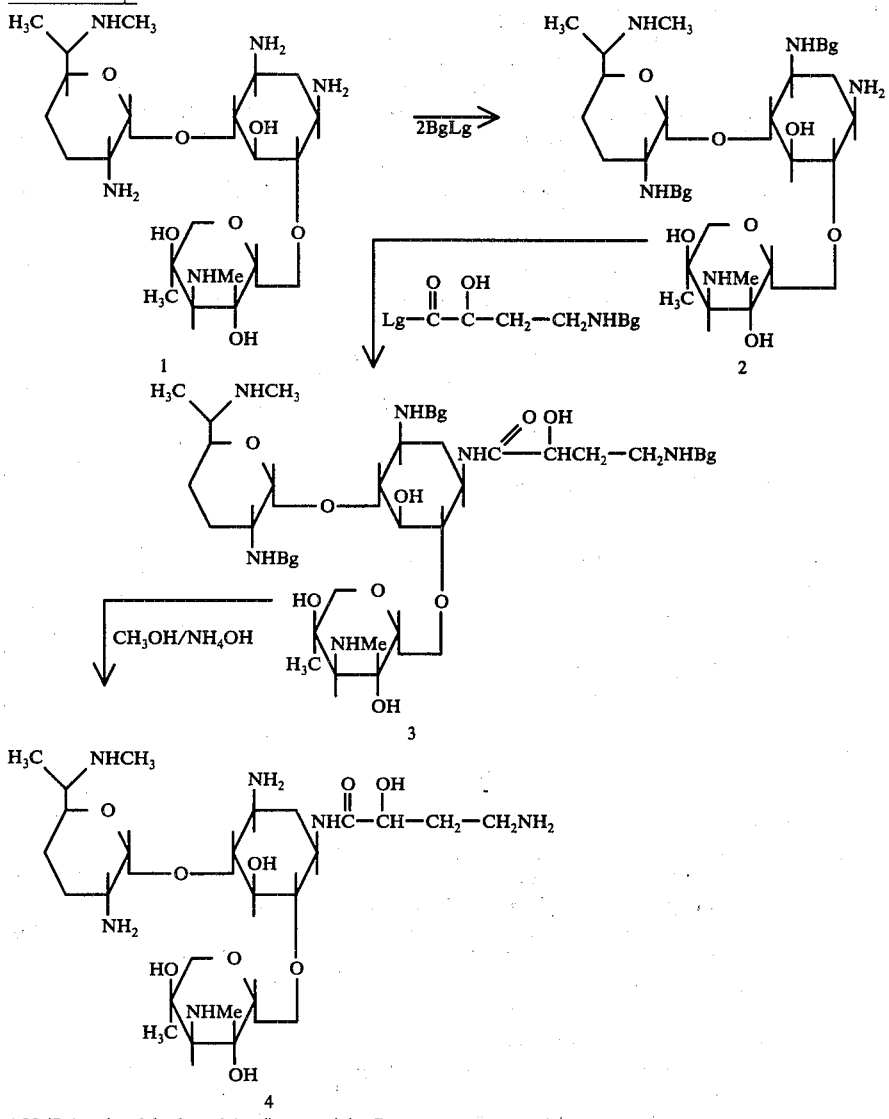

1-N-(S-4-amino-2-hydroxybutyrl)gentamicin $C_1$
wherein BgLg is ethylthioltrifluoroacetate.

Reaction Sequence 2
Sisomicin
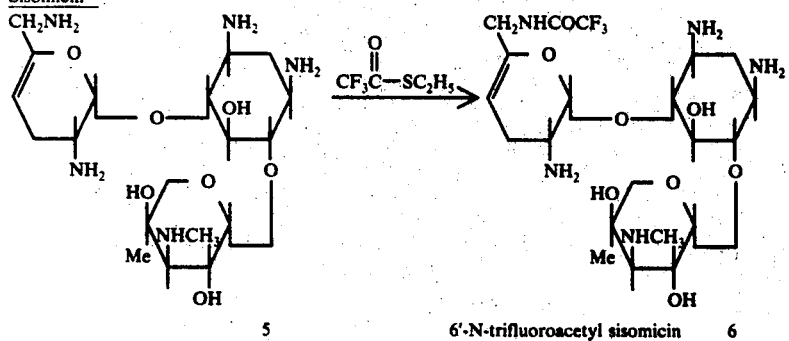
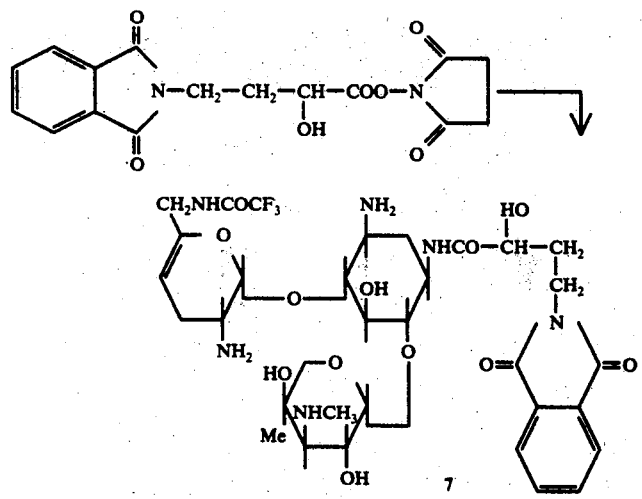
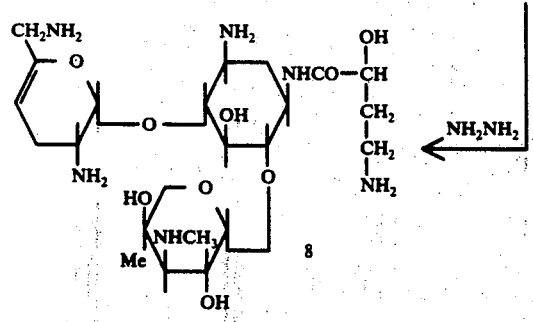
1-N-(S-4-amino-2-hydroxybutyryl)sisomicin
Reaction Sequence 3
Gentamicin B
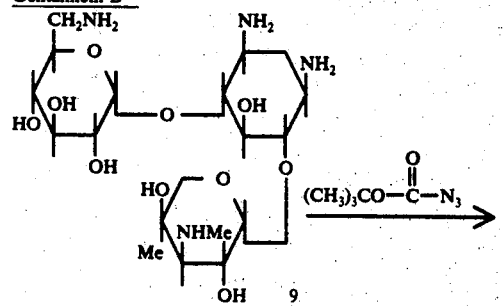
-continued
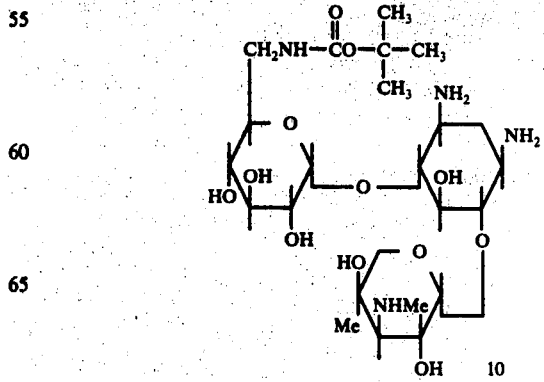

Reaction Sequence 3

Gentamicin B

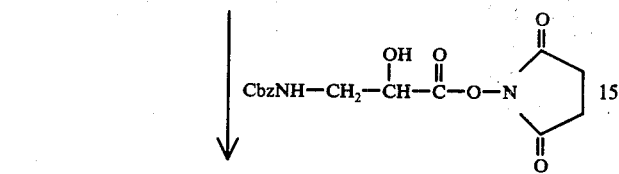

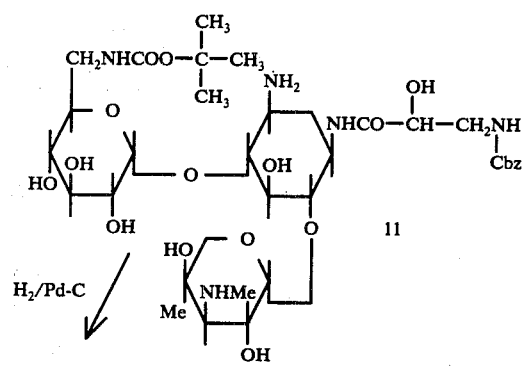

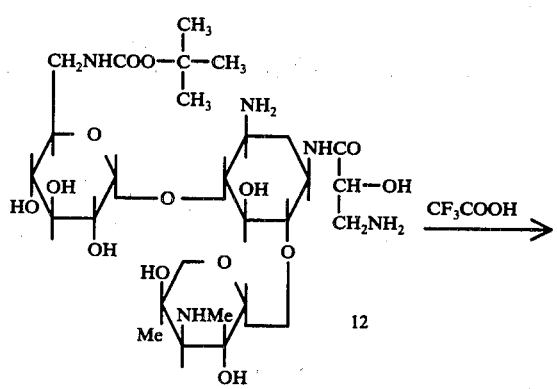

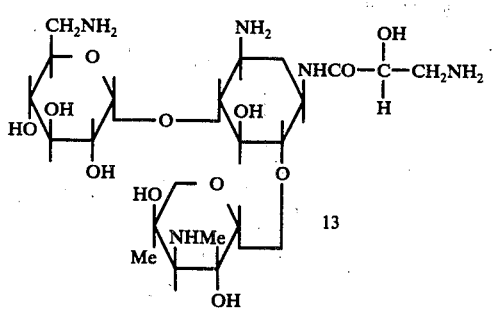

1'-N-(S-3-amino-2-hydroxypropionyl)gentamicin B

Reaction Sequence 4
Verdamicin

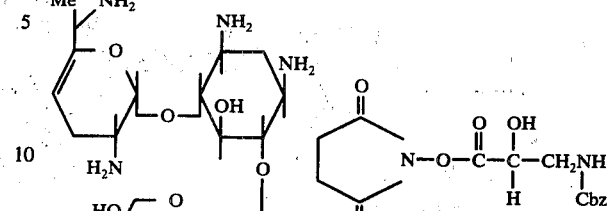

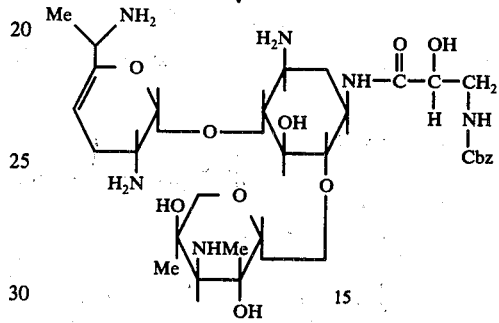

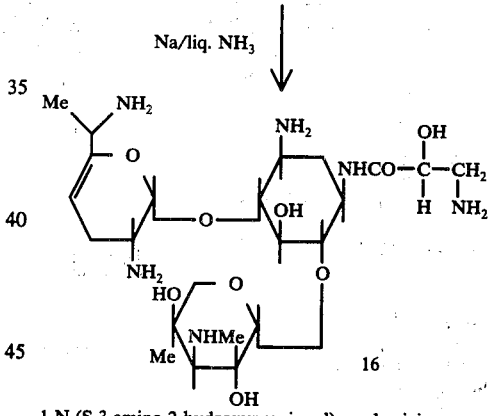

1-N-(S-3-amino-2-hydroxypropionyl) verdamicin

The foregoing reaction sequences exemplify some of the processes which may be employed to prepare the compounds of this invention.

Reaction Sequence 1 describes a process wherein an aminoglycoside antibiotic (gentamicin $C_1$) is reacted with a blocking agent e.g. ethylthioltrifluoroacetate to yield a 2',3-blocked derivative which in turn is treated with a blocked hydroxyaminobutyrylating agent. The product of the latter reaction upon treatment with methanolic ammonium hydroxide yields the desired 1-N-hydroxyaminoacyl derivative.

Reaction Sequence 2 starting with sisomicin describes a process wherein only the 6'-amino is blocked prior to treatment with a blocked hydroxyaminoacylating agent. Again the product of the latter reaction is deblocked under basic conditions, this time with hydrazine.

Reaction Sequence 3 starting with gentamicin B exemplifies the utilization of a t-butoxycarbonyl blocking group to protect the 6'-amino moiety which may then be reacted with a hydroxyaminoacylating agent. In this procedure the hydroxyaminoacyl group is exposed via hydrogenolysis, the 6'-amino moiety being liberated under acidic conditions to yield the desired compound.

Reaction Sequence 4 starting with verdamicin exemplifies the preparation of 1-N-(S-3-amino-2-hydroxypropionyl)verdamicin by direct acylation followed by deblocking using sodium in liquid ammonia. These methods or simple insubstantial modifications thereof may be employed to prepare the compounds of this invention from aminoglycoside antibiotics derived from the fermentation of Actinomycetes.

EXAMPLE 1

1-N-(S-4-Amino-2-hydroxybutyryl)sisomicin

A. S-4-Trifluoroacetamido-2-Hydroxybutyric Acid

Dissolve 5 g of S-4-benzyloxycarbonylamino-2-hydroxybutyric acid in a mixture of 80 ml of dioxane and 20 ml of water. Add 200 mg of 30% palladium - on - carbon and hydrogenate at ambient temperature and 50 p.s.i. for 3 hours. Remove the catalyst by filtration and concentrate the filtrate to a residue in vacuo. Dry the residue in high vacuum for 72 hours. Dissolve the dried residue in 30 ml of cold trifluoroacetic anhydride with agitation. Stir the solution for 3 hours at ambient temperature then concentrate in vacuo to a residue. Triturate the residue with benzene and obtain a grey solid which is isolated by filtration, washed with benzene and dried to give the product of this step.

B. N-(S-4-Trifluoroacetamido-2-hydroxybutyryloxy)succinimide

Dissolve 20 m moles of the product of step A in 50 ml of ethyl acetate, add 2.31 g of N-hydroxysuccinimide with agitation and cool the resulting solution in an ice bath. Add 4.3 g of dicyclohexylcarbodiimide to the solution and stir the reaction mixture for 3 hours at room temperature. Filter to remove the precipitate and concentrate the filtrate to dryness thereby yielding the title product which is dried in high vacuum and used in step D.

C. 6'-N-Trifluoroacetylsisomicin

Dissolve 20 g of sisomicin in 1.2 liters of anhydrous methanol and add dropwise a solution of 6 ml of ethyl thioltrifluoroacetate in 60 ml of methanol over a 3 hour period with stirring. Allow the reaction to proceed for 18 hours at room temperature and remove the solvent in vacuo to give a residue of 23.8g of product of approximately 95% purity having the following physicochemical properties:

Mass Spectral data: m/e 543 M+, other definitive peaks at m/e 413, 395, 385, 362, 223, and 126.

NMR (60MHz, D$_2$O) δ 5.37 doublet, J=2Hz, H-1'; 5.12 doublet, J=4Hz, H-1"; 4.96 broad singlet, H-4'; 2.57, singlet, N—CH$_3$; 1.26 singlet, C—CH$_3$ D. 1-N-(S-4-amino-2-hydroxybutyryl)sisomicin Dissolve 814 mg (1.5 m moles) of 6'-N-trifluoroacetyl sisomicin in 12 ml of 50% aqueous methanol and add dropwise with stirring a solution of 1.5 m moles of the product of Step B dissolved in 3 ml of dimethylformamide. Stir the resulting mixture at room temperature for 18 hours and concentrate in vacuo to a residue. Dissolve the residue in 10 ml of concentrated ammonium hydroxide and allow to stand for 2 hours (to remove the trifluoroacetyl groups). Evaporate the solvent to obtain the title product as a residue. Chromatograph the residue on a silica gel column using the lower phase of a chloroform, methanol, ammonium hydroxide (2:1:1) solvent system as eluant. Fractions containing the title product are pooled and concentrated to a residue which is dissolved in water and lyophilized to yield an amorphous white solid.

In a manner similar to that described in Example 1C, treat each of the following antibiotics with ethylthioltrifluoroacetate in methanol:
gentamicin C$_{1a}$,
gentamicin B,
antibiotic JI-20A,
antibiotic 66-40B,
antibiotic 66-40D, Isolate the resultant products in a manner similar to that described in Example 1C to obtain, respectively:
6'-N-trifluoroacetyl gentamicin C$_{1a}$,
6'-N-trifluoroacetyl gentamicin B,
6'-N-trifluoroacetyl antibiotic JI-20A,
6'-N-trifluoroacetyl antibiotic 66-40B,
6'-N-trifluoroacetyl antibiotic 66-40D, Subject the foregoing 6'-N-trifluoroacetyl intermediates to the procedure of Example 1, step D and obtain thereby the following:
1-N-(S-4-amino-2-hydroxybutyryl)gentamicin C$_{1a}$,
1-N-(S-4-amino-2-hydroxybutyryl)gentamicin B,
1-N-(S-4-amino-2-hydroxybutyryl)antibiotic JI-20A,
1-N-(S-4-amino-2-hydroxybutyryl)antibiotic 66-40B, and
1-N-(S-4-amino-2-hydroxybutyryl)antibiotic 66-40D.

In an analogous manner, by substituting an equivalent quantity of S-3-benzyloxycarbonylamino-2-hydroxypropionic acid or of S-5-benzyloxycarbonylamino-2-hydroxypentanoic acid for S-4-benzyloxycarbonylamino-2-hydroxybutyric acid in Example 1, and by following the procedure of Example 1, the following compounds may be prepared:
1-N-(S-3-amino-2-hydroxypropionyl)sisomicin,
1-N-(S-3-amino-2-hydroxypropionyl)gentamicin C$_{1a}$,
1-N-(S-3-amino-2-hydroxypropionyl)gentamicin B,
1-N-(S-3-amino-2-hydroxypropionyl)antibiotic JI-20A,
1-N-(S-3-amino-2-hydroxypropionyl)antibiotic 66-40B, and
1-N-(S-3-amino-2-hydroxypropionyl)antibiotic 66-40D.
1-N-(S-5-amino-2-hydroxypentanoyl)sisomicin,
1-N-(S-5-amino-2-hydroxypentanoyl)gentamicin C$_{1a}$,
1-N-(S-5-amino-2-hydroxypentanoyl)gentamicin B,
1-N-(S-5-amino-2-hydroxypentanoyl)antibiotic JI-20A,
1-N-(S-5-amino-2-hydroxypentanoyl)antibiotic 66-40B, and
1-N-(S-5-amino-2-hydroxypentanoyl)antibiotic 66-40D.

EXAMPLE 2

1-N-(S-4-amino-2-hydroxybutyryl)gentamicin C$_1$

A. 2'-N-Trifluoroacetyl Gentamicin C$_1$

Dissolve 1.7 g. of gentamicin C$_1$ in 20 ml. of methanol, cool the mixture to 4° C. and add 0.46 ml. (0.563 g.) of ethyl thioltrifluoroacetate with stirring. Allow the reaction to continue for 2 hours and concentrate the solution to a residue in vacuo. Chromatograph the product on 80 g. of silica gel G using the lower phase of a mixture of chloroform, methanol, water, ammonium hydroxide in the volume ratio of 10:5:4:1 as eluant. Combine the fractions containing the major component and concentrate to obtain 1.4 g. of the title compound, m.p. 108°–111° C., $[\alpha]_D^{26°} = +128°$ ($c=0.3\%$, $H_2O$). Analysis for $C_{23}H_{42}N_5O_8F_3.H_2O$ requires C=46.69%; H=7.50%; N=11.84%; F=9.63%. Found: C=46.66%; H=7.65%; N=11.60%; F=9.24%.

B. 2′,3-Di-N-Trifluoroacetyl Gentamicin $C_1$

Dissolve 0.66 g of the product of step 1 in 10 ml of methanol, cool the mixture to 4° C. and add 0.148 ml (0.182 g) of ethyl thioltrifluoroacetate dissolved in 3 ml of methanol. Stir the reaction mixture for about 16 hours and concentrate to a residue in vacuo. Chromatograph the product on 30 g of silica gel as described in Step A. Monitor the column by thin layer chromatography, combine the appropriate fractions and concentrate to obtain 0.32 g of the title compound, m.p. 121°–129° C., $[\alpha]_D^{26°} = 121°$ ($c = 0.3\%$; $H_2O$). Analysis for $C_{25}H_{41}N_5O_9F_6$ requires C=44.84%; H=6.17%; N=10.46%. Found: C=44.94%; H=6.35%; N=10.17%.

C. 1-N-(S-4-Carbobenzyloxyamino-2-hydroxybutyryl)-2′,3-Di-N-trifluoroacetylgentamicin $C_1$ Dissolve 1.12 g of the product of step B in 50 ml of tetrahydrofuran with stirring. Add 0.73 g of the N-hydroxysuccinimide ester of S-4-benzyloxycarbonylamino-2-hydroxy-butyric acid dissolved in 7 ml of tetrahydrofuran. Stir the reaction mixture at room temperature for about 24 hours. Concentrate the solution in vacuo to a residue and chromatograph the product on silica gel using the lower phase of the solvent system chloroform, methanol, 10% ammonium hydroxide in the volume ratio of 2:1:1. Combine the appropriate fractions and concentrate to obtain 1.4 g of the title compound. M.P. 115°–120° C., $[\alpha]_D^{26°} + 80°$ ($c = 0.35$, $CH_3OH$) Analysis calculated for $C_{37}H_{54}N_6O_{13}F_6$: C, 49.11; H, 6.02; N, 9.29%; Found: C,49.26; H, 6.15; N, 8.73%.

D. 1-N-(S-4-amino-2-hydroxybutyryl)gentamicin $C_1$

Dissolve 1.9 g of 1-N-(S-4-benzyloxycarbonylamino-2-hydroxybutyryl)-2′,3-di-N-trifluoroacetylgentamicin $C_1$ in 200 ml of methanol and add 100 ml of concentrated ammonium hydroxide. Stir the solution for 3 days at room temperature at which time thin layer chromatography reveals the complete transformation of the starting material. Evaporate the solution to dryness in vacuo and obtain thereby 1-N-(S-4-benzyloxycarbonylamino-2-hydroxybutyryl)gentamicin $C_1$. Dissolve this residue in 30 ml of acetic acid, add 0.5 g of 10% palladium on carbon catalyst and hydrogenate the solution at 60 p.s.i. for 2½ days. Remove the catalyst by filtration and evaporate the solution to a residue. Chromatograph the residue on a column containing 45 g of silica gel using the lower phase of a chloroform-methanol-concentrated ammonium hydroxide (2:1:1) solvent system as eluant. Monitor the eluate by TLC and combine those fractions containing the major component as a single spot to obtain thereby 1-N-(S-4-amino-2-hydroxybutyryl)gentamicin $C_1$, yield = 0.503 g, m.p. 103°–110°; $[\alpha]_D^{26°} + 101°$ ($c = 0.45$, $H_2O$): PMR (100 MHz, $D_2O$) δ 1.01 (3H, d, J=7Hz, $\underline{CH_3}$-C), 1.17(3H, s, $\underline{CH_3}$-C), 2.32(3H, s, $\underline{CH_3}$-N), 2.47(3H, s, $\underline{CH_3}$-N), 4.19 (1H, t, J=4.2 Hz, H-2‴), 5.08 (1H, d, J=4.5Hz, H-1″), 5.13(1H, d, J=4Hz, H-1′)PPM. Analysis calculated for $C_{25}H_{50}N_6O_9.2H_2O$: C, 48.84; H, 8.85; N, 13.67; Found: C, 48.81; H, 8.65; N, 14.02%.

Alternatively, steps A and B of the foregoing example may be combined as follows: Dissolve 4.95 g. of Gentamicin $C_1$ in 100 ml of methanol at about 25° C. and add dropwise 4.05 g. of ethylthioltrifluoroacetate to the solution with stirring. Continue stirring overnight, concentrate the mixture to a residue in vacuo and chromatograph as described in step B to obtain the title compound of step B which upon being subjected to the procedures of steps C and D would also yield 1-N-(S-4-amino-2-hydroxybutyryl)gentamicin $C_1$.

EXAMPLE 3

1-N-(S-4-amino-2-hydroxybutyryl)sisomicin

Dissolve 1.6 g. of 6′-N-trifluoroacetylsisomicin (prepared as described in Example 1, step C) in a mixture consisting of water (10 ml) and methanol (5 ml). Add a solution of N-(S-4-phthalimido-2-hydroxybutyryloxy)-succinimide (3 m moles) in dimethylformamide (3 ml). Stir the mixture at room temperature for 3 hr. Evaporate the solvent in vacuo, dissolve the residue in ethanol (15 ml) and add hydrazine hydrate (0.3 g). Heat the solution under reflux for 3 hr. and then evaporate the solution in vacuo to a residue. Chromatograph the residue on silica gel (50 g) using the lower phase of a chloroform-methanol-concentrated ammonium hydroxide (2:1:1) solvent system as eluant. Monitor the fractions by TLC and pool fractions containing the pure major component with mobility less than sisomicin. Yield 250 mg.

EXAMPLE 4

A. 6′-N-t-butoxycarbonylgentamicin $C_{1a}$

Dissolve 2.69 g. of gentamicin $C_{1a}$ in 60 ml of methanol-water (1:1), cool to 5° C. and add 1.815 ml of triethylamine. Add with stirring 1.91 g of t-butoxycarbonyl azide dropwise. Stir the mixture at 5° C. for 18 hours. Add 20 ml of Amberlite IRA-401S resin ($O^⊖H$ form), stir for 30 minutes, filter and evaporate the filtrate to dryness in vacuo. Chromatograph the crude product over silica gel (350 g) using the lower phase of a 2:1:1, chloroform: methanol: concentrated ammonium hydroxide solvent system as eluant. Take 3 ml fractions and monitor their contents by TLC. Combine fractions containing the major reaction product and evaporate to obtain the title compound of this example (0.42 g, 13%), $[\alpha]_D^{26°} + 137°$ (MeOH), PMR δ 1.23 (3H, s, C—$CH_3$), 1.45 (9H, s, C—$(CH_3)_3$), 2.53 (3H, s, N—$CH_3$) δ 5.08 (2H, overlapping doublets, J≈3.5Hz, H-1′ and H-1″) PPM. Mass spectrum m/e 550 [(M+1)+] and m/e 549 ($M^{30}$).

Treat 6′-N-t-butoxycarbonylgentamicin $C_{1a}$ to the procedure of the following example (Example 5) steps B and C to obtain 1-N-(S-4-amino-2-hydroxybutyryl)-gentamicin $C_{1a}$.

EXAMPLE 5

1-N-(S-4-Amino-2-hydroxybutyryl) gentamicin B

A. 6′-N-t-butoxycarbonylgentamicin B

Dissolve 1 g of gentamicin B in 30 ml of 50% aqueous methanol and cool to 5° C. Add 0.297 g of t-butoxycarbonyl azide dropwise with stirring followed by 0.186 ml of triethylamine and stir the resulting solution for 18 hours. Evaporate the reaction mixture in vacuo to a residue and chromatograph the residue on 100 g of silica gel using the lower phase of a 2:1:1, chloroform: methanol: concentrated ammonium hydroxide solvent system as eluant. Collect 2 ml fractions and monitor the column effluent by TLC. Combine fractions containing like material (fracts. 180-230) and evaporate to obtain 0.830 g 6'-N-t-butoxycarbonyl gentamicin B having the following physical constants: PMR (60MHz, $D_2O$) δ 1.21(3H, s, C—$CH_3$), 1.42 (9H, s, C($CH_3$)$_3$), 2.53 (3H, s, N—$CH_3$), 5.2 (1H, d, J=4.5Hz, H-1") 5.23 (1H, d, J=3.0 Hz, H-1') PPM.

B.
1-N-(S-4-amino-2-hydroxybutyryl)-6'-N-t-butoxycarbonyl gentamicin B

Dissolve 0.582 g of 6'-N-t-butoxycarbonyl gentamicin B in 25 ml of methanol: water (1:3). Add a solution of 0.334 g of N-(S-4-carbobenzyloxyamino-2-hydroxybutyryloxy) succinimide in 5 ml of dimethylformamide dropwise with agitation. Stir the reaction mixture at 5° C. for 5 hours then evaporate to dryness in vacuo. Chromatograph the residue on 60 g silica gel using the lower phase of a 2:1:1 chloroform: methanol: ammonium hydroxide solvent system as eluant. Collect 3 ml fractions and monitor the content thereof by TLC. Combine fractions 160-235 and evaporate to a residue of 0.280 g migrating as a single spot on TLC. Dissolve the residue in 8 ml of methanol and 10 ml of water and hydrogenate at 55 p.s.i. over 60 mg of 5% palladium on charcoal catalyst. Remove the catalyst by filtration, evaporate the filtrate to a residue and chromatograph on 20 g of silica gel using the lower phase of a 1:1:1 chloroform: methanol: ammonium hydroxide solvent system as eluant. Combine fractions 79-127 (2 ml each) consisting of 1-N-(S-4-amino-2-hydroxybutyryl)-6'-N-t-butoxycarbonyl gentamicin B. Yield 86 mg. PMR δ1.21 (3H, s, C-$CH_3$), 1.43 (9H, s, C-($CH_3$)$_3$), 2.51 (3H, s, N-$CH_3$), 5.08 (1H, d, J=4 Hz, H-1"), 5.25 (1H, d, J=3.5 Hz, H-1') PPM.

C. 1-N-(S-4-Amino-2-hydroxybutyryl)gentamicin B

Dissolve the product of Step B in 0.3 ml of trifluoroacetic acid and after 5 minutes add 30 ml of ethyl ether. A precipitate of the compound of this example as its trifluoroacetate salt forms and is recovered by filtration. Dissolve the precipitate in water and pass the solution through a basic ion exchange resin column in the hydroxide ion form to convert the acid addition salt to the free base. Lyophilize the column effluent to yield the compound of this example as a white amorphous acid. Yield 72 mg.

In a similar manner, by substituting an equivalent quantity of other aminoglycoside aminocyclitol antibiotics, such as gentamicin $C_{1a}$, or antibiotic JI-20A, and by following the procedure of Example 5, step A, the following compounds may be prepared:

6'-N-t-butoxycarbonylgentamicin $C_{1a}$, and
6'-N-t-butoxycarbonyl antibiotic JI-20A.

Similarly, by subjecting the foregoing compounds to the procedures of Example 5, steps B and C, the following compounds may be prepared:

1-N-(S-4-amino-2-hydroxybutyryl)gentamicin $C_{1a}$, and

1-N-(S-4-amino-2-hydroxybutyryl)antibiotic JI-20A.

In an analogous manner, by substituting an equivalent quantity of N-(S-3-carbobenzyloxyamino-2-hydroxypropionyloxy) succinimide or of N-(S-5-carbobenzyloxyamino-2-hydroxypentanoyloxy) succinimide for N-(S-4-carbobenzyloxyamino-2-hydroxybutyryloxy) succinimide in Example 5, step B, by reacting the 6'-N-t-butoxycarbonyl antibiotics therewith and by subjecting the products obtained thereby to the procedure of Example 5, step C, the following compounds may be prepared:

1-N-(S-3-amino-2-hydroxypropionyl)gentamicin B,
1-N-(S-3-amino-2-hydroxypropionyl)gentamicin $C_{1a}$,
1-N-(S-3-amino-2-hydroxypropionyl)antibiotic JI-20A,
1-N-(S-5-amino-2-hydroxypentanoyl)gentamicin B,
1-N-(S-5-amino-2-hydroxypentanoyl)gentamicin $C_1a$, and
1-N-(S-5-amino-2-hydroxypentanoyl)antibiotic JI-20A.

EXAMPLE 6

1-N-(S-3-Amino-2-hydroxypropionyl)gentamicin $C_1$

A.
1-N-(S-3-carbobenzyloxyamino-2-hydroxypropionyl)-2'-3-di-N-trifluoroacetylgentamicin $C_1$ Dissolve 0.84 g of 2',3-di-N-trifluoroacetyl gentamicin $C_1$ (prepared as described in Example 2, Step B) in 40 ml of tetrahydrofuran and add a solution of 1.19 g of N-(S-3-carbobenzyloxyamino-2-hydroxypropionyloxy)succinimide in 24 ml of tetrahydrofuran dropwise with stirring. Stir the reaction mixture for 24 hours then evaporate to a residue. Chromatograph the residue on silica gel using the lower phase of a chloroform: methanol: conc. ammonium hydroxide: water (2:1:0.2:0.8) v/v solvent system as eluant. Monitor the chromatogram by TLC and combine fractions containing like product to obtain the major product of the reaction having the following constants: MP 125°-131° C., $[\alpha]_D^{26} = +93°$ ($CH_3OH$) Anal: Calc. (for dihydrate) C=47.47; H=6.20; N=9.23% Found: C=47.85; H=6.67; N=9.08%.

B.
1-N-(S-3-Carbobenzyloxyamino-2-hydroxypropionyl)-gentamicin $C_1$

Dissolve 0.55 g of the product of Step A in 55 ml of methanol and add 25 ml of concentrated ammonium hydroxide with stirring. Stir for 3 days, at which time T.L.C. on silica gel plates using the lower phase of a 1:1:1 mixture of a chloroform: methanol:concentrated ammonium hydroxide solvent system as developer indicates substantially complete removal of the trifluoroacetyl blocking groups. Evaporate the solution to dryness in vacuo. Yield 0.2 g; M.P. 109°-112° C.; $[\alpha]_D^{26} = +73°$ ($H_2O$)

C. 1-N-(S-3-Amino-2-hydroxypropionyl)gentamicin $C_1$

Dissolve 0.153 g of the residue from step B in 8 ml of acetic acid and add 0.05 g of 10% palladium on carbon catalyst. Hydrogenate the solution at 60 p.s.i. and at 25° C. until T.L.C. (using the solvent system used in Step B) indicates the complete conversion to the title product (i.e. 16 hours→3 days). Remove the catalyst by filtration and evaporate the solution to a residue in vacuo. Chromatograph the residue over 7 g. of silica gel using the lower phase of a 2:1:1 mixture of chloroform: methanol: ammonium hydroxide as eluant. Monitor the column using TLC, combine like materials and obtain thereby the product of this example. Yield 112 mg M.P.

109°–119° C., $[\alpha]_D^{26°} = +98°$ ($H_2O$) Anal. Calc: (monohydrate) C=49.47; H=8.65; N=14.42% Found: C=49.24; H=8.53; N=14.10%

EXAMPLE 7

1-N-(S-4-Amino-2-hydroxybutyryl)verdamicin

A. 1-N-(S-4-Phthalimido-2-hydroxybutyryl)verdamicin

Dissolve 4.61 g of verdamicin in 50 ml of a methanol-water (1:3) solution and cool to 0°–5° C. Add a solution of 3.81 g of N-(S-4-phthalimido-2-hydroxybutyryloxy)succinimide in 20 ml dimethylformamide dropwise with stirring to the antibiotic solution. Stir for an additional 16 hours then concentrate to a residue in vacuo. Chromatograph the residue on a 250 g silica gel column using the lower phase of a 2:1:1 mixture of chloroform: methanol:concentrated ammonium hydroxide as the eluant. Monitor the eluate by TLC and combine fractions containing like materials. Evaporate the combined fractions containing the major product to obtain thereby 1-N-(S-4-phthalimido-2-hydroxybutyryl)verdamicin and an isomer thereof.

B. 1-N-(S-4-Amino-2-hydroxybutyryl)verdamicin

Dissolve 4.0 g of the product of the foregoing step in 35 ml of ethanol and add 1.0 g of hydrazine hydrate. Reflux the solution for 3 hours, then evaporate to dryness in vacuo. Chromatograph the residue over 160 g of silica gel, eluting with the lower phase of a 1:1:1 (v/v) mixture of chloroform:methanol: concentrated ammonium hydroxide. Combine and evaporate the fractions which contain the major component of the reaction as demonstrated by TLC to obtain the compound of this example as a white amorphous solid.

In a similar manner, subject to the process described in Example 7 the following antibiotics:
gentamicin A,
gentamicin $B_1$,
gentamicin $C_2$,
gentamicin $C_{2a}$,
gentamicin X,
antibiotic G-418,
antibiotic JI-20B, and
antibiotic G-52.

Isolate the resultant products in the manner described in Example 7 to obtain respectively:
1-N-(S-4-amino-2-hydroxybutyryl)gentamicin A,
1-N-(S-4-amino-2-hydroxybutyryl)gentamicin $B_1$,
1-N-(S-4-amino-2-hydroxybutyryl)gentamicin $C_2$,
1-N-(S-4-amino-2-hydroxybutyryl)gentamicin $C_{2a}$,
1-N-(S-4-amino-2-hydroxybutyryl)gentamicin X,
1-N-(S-4-amino-2-hydroxybutyryl)antibiotic G-418,
1-N-(S-4-amino-2-hydroxybutyryl)antibiotic JI-20B, and
1-N-(S-4-amino-2-hydroxybutyryl)antibiotic G-52.

In an analogous manner, by substituting an equivalent quantity of N-(S-3-phthalimido-2-hydroxypropionyloxy)succinimide, or of N-(S-5-phthalimido-2-hydroxypentanoyloxy)succinimide for the N-(S-4-phthalimido-2-hydroxybutyryloxy)succinimide and by following the process described in Example 7, the 1-N-(S-3-amino-2-hydroxypropionyl) and/or 1-N-(S-5-amino-2-hydroxypentanoyl derivatives of the foregoing antibiotics may be prepared. Accordingly, using N-(S-3-phthalimido-2-hydroxypropionyloxy) succinimide or N-(S-5-phthalimido-2-hydroxypentanoyl)succinimide in step A, subject the following antibiotics to the process of Example 7:
verdamicin,
gentamicin A,
gentamicin $B_1$,
gentamicin $C_2$,
gentamicin $C_{2a}$,
gentamicin X,
antibiotic G-418,
antibiotic JI-20B, and
antibiotic G-52.

Isolate the resultant products in the manner described in Example 7 to obtain, respectively:
1-N-(S-3-amino-2-hydroxypropionyl)verdamicin,
1-N-(S-3-amino-2-hydroxypropionyl)gentamicin A,
1-N-(S-3-amino-2-hydroxypropionyl)gentamicin $B_1$,
1-N-(S-3-amino-2-hydroxypropionyl)gentamicin $C_2$,
1-N-(S-3-amino-2-hydroxypropionyl)gentamicin $C_{2a}$,
1-N-(S-3-amino-2-hydroxypropionyl)gentamicin X,
1-N-(S-3-amino-2-hydroxypropionyl)antibiotic G-418,
1-N-(S-3-amino-2-hydroxypropionyl)antibiotic JI-20B,
1-N-(S-3-amino-2-hydroxypropionyl)antibiotic G-52,
1-N-(S-5-amino-2-hydroxypentanoyl)verdamicin,
1-N-(S-5-amino-2-hydroxypentanoyl)gentamicin A,
1-N-(S-5-amino-2-hydroxypentanoyl)gentamicin $B_1$,
1-N-(S-5-amino-2-hydroxypentanoyl)gentamicin $C_2$,
1-N-(S-5-amino-2-hydroxypentanoyl)gentamicin $C_{2a}$,
1-N-(S-5-amino-2-hydroxypentanoyl)gentamicin X,
1-N-(S-5-amino-2-hydroxypentanoyl)antibiotic G-418,
1-N-(S-5-amino-2-hydroxypentanoyl)antibiotic JI-20B, and
1-N-(S-5-amino-2-hydroxypentanoyl)antibiotic G-52.

EXAMPLE 8

N-(S-3-t-Butoxycarbonylamino-2-hydroxypropionyloxy)succinimide

A. S-3-t-Butoxycarbonylamino-2-hydroxypropionic acid

Dissolve 8.0 g of S-3-carbobenzyloxyamino-2-hydroxypropionic acid in 110 ml of dioxane-water (4:1). Add 200 mg of palladium on carbon catalyst and hydrogenate at 50 psi for 3 hr. Filter off the catalyst and evaporate the filtrate to a residue comprising S-3-amino-2-hydroxypropionic acid. Dissolve the acid in methanol (40 ml) and triethylamine (8.5 ml), cool the solution in an ice-bath and add t-butoxycarbonyl azide (4.76 g). Allow the mixture to stand overnight with gradual warming to room temperature. Evaporate most of the methanol, dilute with water and acidify with dilute hydrochloric acid to pH 3. Extract the aqueous mixture several times with ethyl acetate, combine and dry the ethyl acetate extracts and evaporate to a residue in vacuo. Recrystallize the residue from ethyl acetate-hexane to give the title compound of this example. Yield = 3.5 g. m.p. 92°–94°, $[\alpha]_D^{26°}$; + 14.9°, (c=0.68, $H_2O$), calculation for $C_8H_{15}NO_5$ requires: C, 46.82; H, 7.37; N, 6.83%. Found: C, 46.81; H, 7.61; N, 6.63%.

B. N-(S-3-t-Butoxycarbonylamino-2-hydroxypropionyloxy)succinimide

Dissolve 2.3 g of S-3-t-butoxycarbonylamino-2-hydroxypropionic acid in a mixture of tetrahydrofuran (25 ml) and ethyl acetate (60 ml). With stirring add 1.42 g of N-hydroxysuccinimide, followed by a solution of dicyclohexylcarbodiimide (2.51 g) in ethyl acetate (10 ml). Allow the mixture to stir for 16 hrs. then filter off the precipitated solids. Evaporate the filtrate to obtain the product of this example. Yield = 3.56 g.

In a similar manner substitute an equivalent quantity of S-4-carbobenzyloxyamino-2-hydroxybutyric acid for the S-3-carbobenzyloxyamino-2-hydroxypropionic acid in Example 8A. Subject this acid to the procedure of Example 8 and obtain N-(S-4-t-butoxycarbonylamino-2-hydroxybutyryloxy)succinimide.

The compounds of this invention are broad spectrum antibacterial agents possessing improved antibacterial activities compared to the parent antibiotics. This improved activity is specifically manifest in the improved activity of the claimed compounds against organisms resistant to the parent compound. Thus, for example, the compounds of this invention are more active against organisms which inactivate the parent antibiotics by acetylation of the 3-amino group and/or by adenylylation of the 2''-hydroxyl group. Thus, the compounds disclosed and claimed herein have the potential of becoming commercially important antibacterial agents and may be employed for the same uses as their underivatized (parent) antibiotics, e.g. they may be used as a bacteriotatic rinse for hospital glassware, surgical instruments, bath tubs or for cleaning areas wherein laboratory animals are housed, or the like.

In addition to their utility as antibacterial agents, the compounds of this invention are useful as intermediates in the preparation of a novel class of compounds which also possess unexpectedly enhanced antibacterial activity. Evidence of this utility may be found in the application of Wright, J. J.; Daniels, P. J. L.; Mallams, A. K. and Nagabhushan, T. L. entitled, "1-N-Alkyl-4,6-di-(aminoglycosyl)-1,3-diaminocyclitols, Methods for Their Manufacture, Methods for Their Use As Antibacterial Agents, and Compositions Useful Therefor." The application bears the Ser. No. 452,600 and was filed concomitantly with the parent of this application.

I claim:

1. A 1-N-X-aminoglycoside anti-bacterial agent selected from the group consisting of 1-N-X-gentamicin A, 1-N-X-gentamicin B, 1-N-X-gentamicin $B_1$, 1-N-X-gentamicin $C_1$, 1-N-X-gentamicin $C_{1a}$, 1-N-X-gentamicin $C_2$, 1-N-X-gentamicin $C_{2a}$, 1-N-X-gentamicin X, 1-N-X-sisomicin, 1-N-X-verdamicin, 1-N-X-antibiotic G-418, 1-N-X-antibiotic 66-40B, 1-N-X-antibiotic 66-40D, 1-N-X-antibiotic JI-20A, 1-N-X-antibiotic JI-20B, 1-N-X-antibiotic G-52 and the pharmaceutically acceptable acid addition salts thereof, wherein X is S-3-amino-2-hydroxypropionyl.

2. A 1-N-X-aminoglycoside anti-bacterial agent selected from the group consisting of 1-N-X-gentamicin A, 1-N-X-gentamicin B, 1-N-X-gentamicin $B_1$, 1-N-X-gentamicin $C_{2a}$, 1-N-X-gentamicin X, 1-N-X-sisomicin, 1-N-X-verdamicin, 1-N-X-antibiotic G-418, 1-N-X-antibiotic 66-40B, 1-N-X-antibiotic 66-40D, 1-N-X-antibiotic JI-20A, 1-N-X-anti-biotic JI-20B, 1-N-X-antibiotic G-52 and the pharmaceutically acceptable acid addition salts thereof, wherein X is S-4-amino-2-hydroxybutyryl.

3. A compound of claim 1, said compound being 1-N-(S-3-amino-2-hydroxypropionyl)sisomicin.

4. A compound of claim 1, said compound being 1-N-(S-3-amino-2-hydroxypropionyl)antibiotic 66-40B.

5. A compound of claim 1, said compound being 1-N-(S-3-amino-2-hydroxypropionyl)antibiotic 66-40D.

6. A compound of claim 1, said compound being 1-N-(S-3-amino-2-hydroxypropionyl)antibiotic G-52.

7. A compound of claim 1, said compound being 1-N-(S-3-amino-2-hydroxypropionyl)verdamicin.

8. A compound of claim 1, said compound being 1-N-(S-3-amino-2-hydroxypropionyl)gentamicin $C_1$.

9. A compound of claim 1, said compound being 1-N-(S-3-amino-2-hydroxypropionyl)gentamicin $C_2$.

10. A compound of claim 1, said compound being 1-N-(S-3-amino-2-hydroxypropionyl)gentamicin $C_{1a}$.

11. A compound of claim 1, said compound being 1-N-(S-3-amino-2-hydroxypropionyl)gentamicin $C_{2a}$.

12. A compound of claim 1, said compound being 1-N-(S-3-amino-2-hydroxypropionyl)gentamicin X.

13. A compound of claim 1, said compound being 1-N-(S-3-amino-2-hydroxypropionyl)gentamicin A.

14. A compound of claim 1, said compound being 1-N-(S-3-amino-2-hydroxypropionyl)gentamicin B.

15. A compound of claim 1, said compound being 1-N-(S-3-amino-2-hydroxypropionyl)gentamicin $B_1$.

16. A compound of claim 1, said compound being 1-N-(S-3-amino-2-hydroxypropionyl)antibiotic JI-20A.

17. A compound of claim 1, said compound being 1-N-(S-3-amino-2-hydroxypropionyl)antibiotic JI-20B.

18. A compound of claim 1, said compound being 1-N-(S-3-amino-2-hydroxypropionyl)antibiotic G-418.

19. A compound of claim 2, said compound being 1-N-(S-4-amino-2-hydroxybutyryl)sisomicin.

20. A compound of claim 2, said compound being 1-N-(S-4-amino-2-hydroxybutyryl)antibiotic 66-40B.

21. A compound of claim 2, said compound being 1-N-(S-4-amino-2-hydroxybutyryl)antibiotic 66-40D.

22. A compound of claim 2, said compound being 1-N-(S-4-amino-2-hydroxybutyryl)antibiotic G-52.

23. A compound of claim 2, said compound being 1-N-(S-4-amino-2-hydroxybutyryl)verdamicin.

24. A compound of claim 2, said compound being 1-N-(S-4-amino-2-hydroxybutyryl)gentamicin $C_{2a}$.

25. A compound of claim 2, said compound being 1-N-(S-4-amino-2-hydroxybutyryl)gentamicin X.

26. A compound of claim 2, said compound being 1-N-(S-4-amino-2-hydroxybutyryl)gentamicin A.

27. A compound of claim 2, said compound being 1-N-(S-4-amino-2-hydroxybutyryl)gentamicin B.

28. A compound of claim 2, said compound being 1-N-(S-4-amino-2-hydroxybutyryl)gentamicin $B_1$.

29. A compound of claim 2, said compound being 1-N-(S-4-amino-2-hydroxybutyryl)antibiotic JI-20A.

30. A compound of claim 2, said compound being 1-N-(S-4-amino-2-hydroxybutyryl)antibiotic JI-20B.

31. A compound of claim 2, said compound being 1-N-(S-4-amino-2-hydroxybutyryl)antibiotic G-418.

32. A 6'-N-trifluoroacetyl derivative of an aminoglycoside antibiotic selected from the group consisting of gentamicin $C_{1a}$, gentamicin B, antibiotic JI-20A, antibiotic 66-40B, antibiotic 66-40D, and sisomicin.

33. A compound of claim 32, said compound being 6'-N-trifluoroacetyl gentamicin $C_{1a}$.

34. A compound of claim 32, said compound being 6'-N-trifluoroacetyl gentamicin B.

35. A compound of claim 32, said compound being 6'-N-trifluoroacetyl antibiotic JI-20A.

36. A compound of claim 32, said compound being 6'-N-trifluoroacetyl antibiotic 66-40B.

37. A compound of claim 32, said compound being 6'-N-trifluoroacetyl antibiotic 66-40D.

38. A compound of claim 32, said compound being 6'-N-trifluoroacetyl sisomicin.

39. A 6'-N-t-butoxycarbonyl derivative of an aminoglycoside antibiotic selected from the group consisting of gentamicin $C_{1a}$, gentamicin B, sisomicin, antibiotic 66-40B, antibiotic 66-40D and antibiotic JI-20A.

40. A compound of claim 39, said compound being 6'-N-t-butoxycarbonyl gentamicin $C_{1a}$.

41. A compound of claim 39, said compound being 6'-N-t-butoxycarbonyl gentamicin B.

42. A compound of claim 39, said compound being 6'-N-t-butoxycarbonyl sisomicin.

43. A compound of claim 39, said compound being 6'-N-t-butoxycarbonyl antibiotic 66-40B.

44. A compound of claim 39, said compound being 6'-N-t-butoxycarbonyl antibiotic 66-40D.

45. A compound of claim 39, said compound being 6'-N-t-butoxycarbonyl antibiotic JI-20A.

46. 2',3-di-N-trifluoroacetylgentamicin $C_1$.

* * * * *